United States Patent [19]

Uda et al.

[11] Patent Number: 5,521,100
[45] Date of Patent: May 28, 1996

[54] METHOD OF DETERMINING THE MOLECULAR WEIGHT DISTRIBUTION OF CARBOXYMETHYLCELLULOSE OR A SALT THEREOF

[75] Inventors: Yukio Uda, Shiga; Shusaku Matsumoto, Kyoto, both of Japan

[73] Assignee: Dai-Ichi Kogyo Seiyaku Co., Ltd., Kyoto, Japan

[21] Appl. No.: 298,867

[22] Filed: Aug. 31, 1994

[30] Foreign Application Priority Data

Sep. 3, 1993 [JP] Japan .................................. 5-219522

[51] Int. Cl.$^6$ .................................. G01N 30/02
[52] U.S. Cl. ........................... 436/161; 210/656; 436/94; 436/128; 436/129; 536/98
[58] Field of Search .................... 436/161, 94, 128–129; 536/98; 210/656

[56] References Cited

U.S. PATENT DOCUMENTS 5,366,755  11/1994  Timonen et al. ....................... 426/658

FOREIGN PATENT DOCUMENTS 3528218  3/1986  Germany .
3261729  11/1991  Japan .

OTHER PUBLICATIONS

Proceedings 5th International Dissolving Pulps Conference, 1980, TAPPI, Atlanta US, pp. 224–228, Agg, G., et al. "The determination of cellulose molecular weight distribution by gel permeation chromatography and its application in pulp and viscose production".

Chemical Abstracts, CA 70:39031. Eriksson et al., "Gel filtration chromatography of hemicelluloses and carboxymethyl cellulose in cadoxen solution," Svensk Papperstidn. 71(19) pp. 695–698 (1968).

Chemical Abstracts, CA 76:61129. Geczy et al., "Determination of the molecular weight distribution of cellulose and carboxymethyl cellulose by turbidimetric titration in cadoxen (cadmium ethylenediamine) solution", Kolor. Ert. 13(9–10) pp. 209–221 (1971).

*Primary Examiner*—Jill Warden
*Assistant Examiner*—Jan M. Ludlow
*Attorney, Agent, or Firm*—Jordan and Hamburg

[57] ABSTRACT

The molecular weight distribution of carboxymethylcellulose or its salt is determined by gel permeation chromatography using a metal-amine complex and/or a metal-alkali complex as the mobile phase solvent. The column geometry (inside diameter/length) and flow rate for this determination are 1:40-100 and 0.2–0.5 ml/min., respectively. According to this method, the GPC determination of molecular weight distribution can be performed under the same conditions for both starting pulp and CMC.

3 Claims, 2 Drawing Sheets

METHOD OF DETERMINING THE MOLECULAR WEIGHT DISTRIBUTION OF CARBOXYMETHYLCELLULOSE OR A SALT THEREOF

BACKGROUND OF THE INVENTION

This invention relates to a method of determining the molecular weight distribution of carboxymethylcellulose or a salt thereof (hereinafter referred to briefly as CMC).

While CMC is conventionally produced from pulp, an efficient quality and process control through its manufacturing stage demands that the conditions of molecular weight distribution analysis of CMC be identical with those of the material pulp.

The molecular weight is generally determined by gel permeation chromatography (hereinafter referred to briefly as GPC).

In the conventional GPC technology for molecular weight distribution analysis, said two determinations (for pulp and CMC) cannot be carried out under identical conditions because pulp and CMC cannot be dissolved within the same time period, the necessary derivatization of pulp complicates the determination procedure and/or the aging of the column packing is rapid and severe, to mention just a few difficulties.

For these reasons, GPC analyses of the molecular weight distributions of pulp and CMC have heretofore been performed using different mobile phase solvents under different conditions, thus presenting the problem that the molecular weight distribution of starting pulp and that of CMC cannot be exactly compared in equal terms.

The conventional GPC determination of starting pulp involves the use of a cascade of 2–3 columns packed with hydrous materials and, as the mobile phase solvent, many solvent species such as an aqueous solution of iron sodium tartrate complex, an aqueous solution of cadoxen, etc. in the case of aqueous systems or paraformaldehyde-dimethyl sulfoxide, etc. in the case of non-aqueous systems.

Incidentally, Graham Agg and coworkers reported in 1980 that they determined the molecular weight distributions of sulfite pulp and PHK pulp by GPC using an aqueous solution of iron sodium tartrate complex as the mobile phase solvent but their samples for analysis were pulps and not CMC (Int. Dissolving Pulps Conf. [Conf. Pap.] 5th, 224–229. TAPPI).

Meanwhile, the GPC analysis of CMC has been performed using 3–4 columns packed with hydrous materials and, as the mobile phase solvent, aqueous solutions of sodium chloride, sodium nitrate, etc.

SUMMARY OF THE INVENTION

The object of this invention is to provide a method by which the molecular weight and molecular weight distribution of CMC can be determined under the same conditions as its starting pulp.

The inventors of this invention did much research to overcome the above-mentioned disadvantages of the prior art and found that these disadvantages can be effectively overcome by employing certain members deliberately selected from a large group of known mobile phase solvents for GPC analysis.

The determination method of this invention is thus characterized in that a solvent containing a metal-amine complex and/or a metal-alkali complex is used in the determination of the molecular weight distribution of CMC.

DETAILED DESCRIPTION OF THE INVENTION

Figure 1:
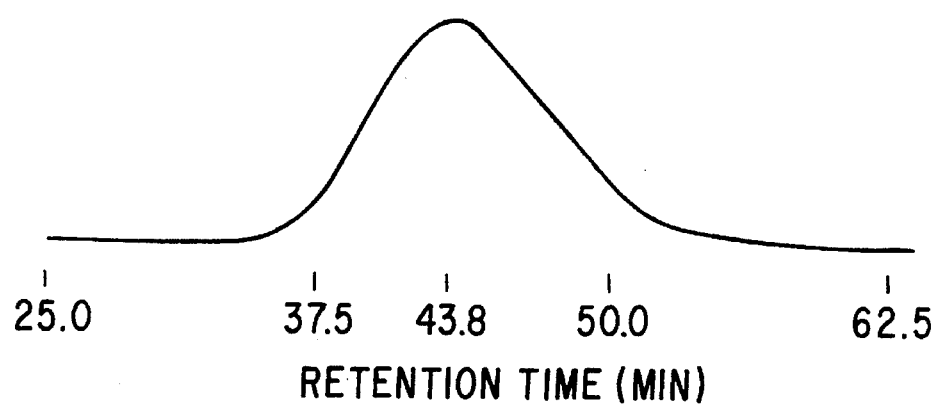
FIG. 1 is a GPC chart of the pulp sample used in Example 1.

The kind of starting pulp that can be analyzed is not critical but includes wood pulp, linter pulp and so on.

The degree of etherification and type of salt that can be dealt with are as mentioned below but not limited thereto. Thus, the degree of etherification may range from 0.2 to 2.8 and the type of salt includes the salts of Na, K, Ca, $NH_4$ and so on.

The mobile phase solvent includes (1) various metal-amine complex solutions, e.g. copper-ethylenediamine solution, cerium-ethylenediamine solution, zinc-ethylenediamine solution, nickel-ethylenediamine solution, cadmium-ethylenediamine solution, etc., and (2) various metal-alkali complex solutions, e.g. copper-ammonium solution, nickel-ammonium solution, iron tartrate-sodium solution and so on.

Particularly preferred, in terms of the solubility of CMC and pulp, are cadmium-ethylenediamine in category (1) and iron tartrate-sodium solution in category (2).

An exemplary procedure for the preparation of one species of the complex solution (1) and of the complex solution (2) is now described.

Cadmium-ethylenediamine solution:

Cadmium oxide and ethylenediamine are dissolved in water and the insoluble matter is removed to provide an aqueous solution of predetermined concentration. The preferred concentrations of ethylenediamine and cadmium in this aqueous solution are 20–40% and 4–15%, respectively.

Iron tartrate-sodium solution:

After iron nitrate, sodium tartrate and sodium hydroxide are mixed in water, ethanol is added. The ethanol-insoluble fraction is separated and dried under reduced pressure to provide iron sodium tartrate. To this iron sodium tartrate are added NaOH and sodium tartrate to provide a solution of predetermined concentration. The preferred concentration of iron sodium tartrate is 200–500 g/l, that of sodium tartrate is 20–70 g/l, and that of NaOH is 10–100 g/l.

Referring to the column, one with an inside diameter-length ratio (hereinafter referred to as column geometry) of 1:40–100 is preferred. In the event of deviation from the above range, determination accuracy and reliability tend to decrease.

The solid phase material of the column is not critical but includes various hydrophilic vinyl polymers. For example, polyvinyl alcohol, TSK-GEL PW series from Tosoh Corporation, e.g. TSK gel G2000PW, TSK gel G3000PW, TSK gel G4000PW, TSK gel G5000PW, TSK gel G6000PW and TSK gel GMPW, and GS-520, GS-620, GS-710 and GSM-700 from Asahi Chemical Industry Co., Ltd. can be mentioned by way of example.

The flow rate per unit time is not critical but preferably 0.2–0.5 ml/minute. With a flow rate of less than 0.2 ml/minute, the reproducibility of analysis is adversely affected, while a flow rate of more than 0.5 ml/min. is undesirable, for it results in an excessive column pressure beyond that tolerated by the column.

By controlling the above-mentioned column geometry and flow rate, the peak values of molecular weight distributions of both pulp and CMC can be easily found and the molecular weight determinations are also facilitated.

The method for computation of average molecular weight (the molecular weight at the centroid dividing the distribution into halves) is now explained.

$$\text{Average molecular weight } (M) = (162 + 80 \times DS) \times K \times [\eta] \quad (1)$$

$[\eta]$: intrinsic viscosity
DS: degree of etherification
K: a constant

First, the average molecular weight (M1) of a first standard pulp (or a first standard CMC) is calculated by means of the above equation (1). In addition, the corresponding retention time (RT1) is measured by GPC and the retention time point (min.) dividing the distribution into halves (at the centroid of the distribution) is determined. The value thus found is multiplied by the flow rate to arrive at the retention volume (Ve1) at the centroid.

Separately but similarly, the average weight molecular weight (M2) of a second standard pulp (or a second standard CMC) is calculated by means of the above equation (1). The corresponding retention time (RT2) is measured by GPC and the retention time point (min.) dividing the distribution into halves is determined. The value thus found is multiplied by the flow rate to arrive at the retention volume (Ve2) at the centroid of distribution.

Using the above-mentioned retention volume (Ve1) determined from average molecular weight (M1) and retention time (RT1) and the retention volume (Ve2) determined from average molecular weight (M2) and retention time (RT2), the parameters a and b of the following equation (2) are determined.

$$\text{Log } M = b + a \times Ve \quad (2)$$

M: average molecular weight
Ve: the retention time point (min.) dividing the distribution into halves x flow rate (ml/min.)

Although a and b can be determined by using at least two standard pulps as described above, it is recommendable to determine a and b using 3 or more, preferably 5–10, different standard pulps for improved accuracy of determination.

Then, the retention time of an unknown sample (pulp or CMC) is measured by GPC and the retention time point (min.) dividing the distribution into halves is determined. Then, Ve is calculated and using the above equation (2) with already known values of a and b, the average molecular weight (molecular weight) of the unknown sample is calculated.

The procedures for preparing samples (CMC and pulp) are briefly described below.

In 10 ml of the mobile phase solvent is dissolved 0.001–0.005 g of CMC or starting pulp. This dissolution of a sample is carried out in a hermetically closed system to avoid evaporation of water (the evaporation of water makes the GPC baseline unstable).

The injection size is not so critical but may generally be 0.5–3 ml.

In accordance with this invention, determination of the molecular weight distribution of starting pulp and that of CMC can be performed under identical conditions. This feature contributes greatly to quality control and process control in the production of CMC.

EXAMPLES

Example 1

[Preparation of an aqueous iron tartrate-sodium solution]
(1) Preparation of iron sodium tartrate complex An aqueous solution prepared by dissolving 324 g of ferric nitrate (nonahydrate) in 600 g of distilled water was blended with an aqueous solution prepared by dissolving 554 g of sodium tartrate (dihydrate) in 1,600 g of distilled water. To this mixture was added 200 g of 40% aqueous solution of sodium hydroxide with stirring.

To this mixture was added about 500 ml of ethanol followed by further stirring. This addition of ethanol caused precipitation of a green-colored water-soluble fraction (A precipitate containing iron sodium tartrate complex).

The upper layer of the above mixture was discarded and the under layer was washed with ethanol a few times and dried under reduced pressure to provide a powder of iron sodium tartrate complex.
(2) Preparation of an iron tartrate-sodium solution In a sufficient amount of distilled water were dissolved 350 g of the above iron sodium tartrate complex, 35 g of sodium tartrate and 40 g of sodium hydroxide to prepare 1 l of an aqueous iron tartrate-sodium solution.

This solution was filtered through a 0.5 μm membrane filter for use as the mobile phase and solvent for samples.
[Preparation of a CMC sample]

The CMC sample was prepared as follows. CMC (Na salt, degree of etherification 0.67) was thoroughly dissolved in a predetermined amount of aqueous iron tartrate-sodium solution to provide a CMC sample of 0.0003 g/ml concentration. This preparation of a sample was carried out in a hermetically closed system for avoiding evaporation of water.
[Preparation of a pulp sample]

The pulp sample was prepared as follows. Thus, pulp (Kojin, wood pulp) was thoroughly dissolved in a predetermined amount of aqueous iron tartrate-sodium solution to provide a CMC sample of 0.0003 g/ml concentration. This preparation of a pulp sample was carried out in a hermetically closed system to avoid evaporation of water.

Prior to GPC determination of the molecular weight distribution of the CMC sample and that of the pulp sample, the retention time values of at least two standard CMC and as many standard pulp samples [the average molecular weights of these standard samples were already known from equation (1)] were measured and the Ve values and equation (2) were determined. The equation (2) thus obtained was Log M=11.40–0.37 Ve.

Thereafter, the retention time values of said CMC sample and pulp sample were measured by GPC. The conditions of analysis are shown in Table 1.

TABLE 1

|  | Example 1 |
| --- | --- |
| Column | TSK gel GMPW |
| Column geometry (in. dia.:length) | 1:80 |
| Flow rate | 0.35 ml/min. |
| Injection size | 1 ml |

It is clear from the GPC chart of the pulp sample that the retention time point dividing the distribution into halves was 43.80 (min.) (FIG. 1).

Figure 2:
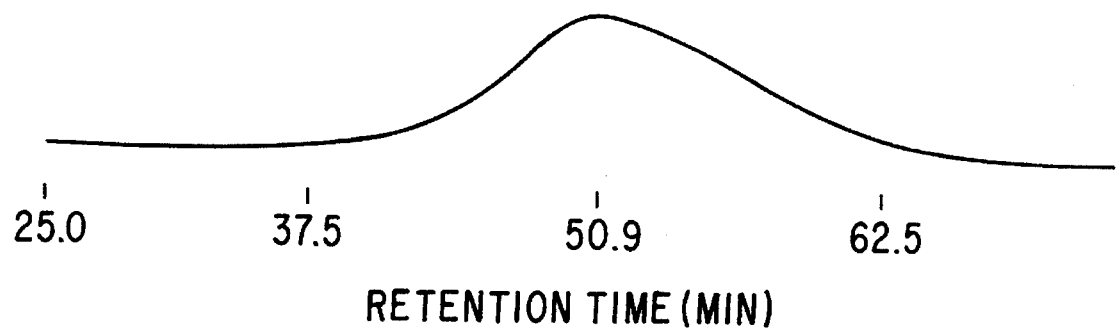
FIG. 2 is a GPC chart of the CMC sample used in Example 1.

It is also clear from the GPC chart of the CMC sample that the retention time point dividing the distribution into halves was 50.90 (min.). (FIG. 2)

Then, Ve was determined and from the value found and equation (2), the average molecular weight of the pulp was found to be 540,000 and that of CMC to be 64,300.

In this manner the GPC determination of molecular weight and molecular weight distribution could be carried out under the same conditions for pulp and CMC.

Comparative Example 1

An attempt was made to dissolve pulp in an aqueous solution of sodium chloride. However, the attempt failed so that this substance could not be used as the mobile phase solvent for pulp.

Example 2

[Preparation of cadmium-ethylenediamine solution]

In 700 g of distilled water was dissolved 300 g of ethylenediamine followed by addition of 120 g of cadmium oxide.

The undissolved cadmium oxide was removed to provide a clear aqueous solution. This solution was filtered through a 0.5 μm membrane filter for use as the mobile phase and solvent for samples.

[Preparation of a CMC sample]

The CMC sample was prepared as follows. Thus, CMC (Na salt, degree of etherification 0.67) was thoroughly dissolved in a predetermined amount of aqueous cadmium-ethylenediamine solution to provide a CMC sample of 0.0003 g/ml concentration. This preparation of a sample was carried out in a hermetically closed system to avoid evaporation of water.

[Preparation of a pulp sample]

The pulp sample was prepared as follows. Thus, pulp (Kojin, wood pulp) was thoroughly dissolved in a predetermined amount of aqueous cadmium-ethylenediamine solution to provide a pulp sample of 0.0003 g/ml concentration. This preparation of a pulp sample was carried out in a hermetically closed system to avoid evaporation of water.

Prior to GPC determination of the molecular weight distribution of the CMC sample and that of the pulp sample, the retention time values of at least two standard CMC and as many standard pulp samples [the average molecular weights of these standard samples were already known from equation (1)] were measured and the Ve values and equation (2) were determined. The equation (2) thus obtained was Log M=14.10−0.53 Ve.

Thereafter, the retention time values of said CMC sample and pulp sample were measured by GPC. The conditions of analysis are the same as in the above Table 1.

Figure 3:
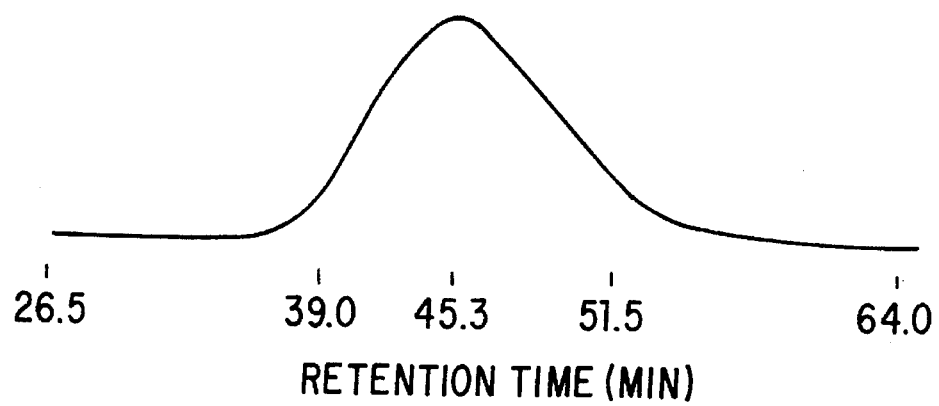
FIG. 3 is a GPC chart of the pulp sample used in Example 2.

It is apparent from the GPC chart of the pulp sample that the retention time point dividing the distribution into halves was 45.29 (min.) (FIG. 3).

Figure 4:
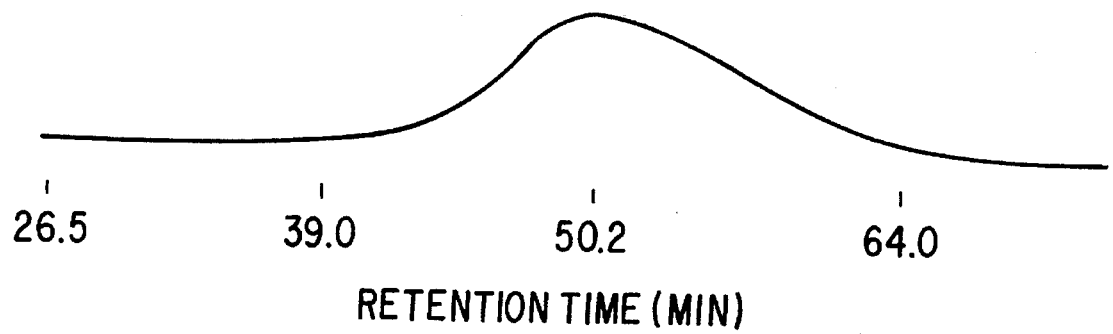
FIG. 4 is a GPC chart of the CMC sample used in Example 2.

It is also clear from the GPC chart of the CMC sample that the retention time point dividing the distribution into halves was 50.21 (min.). (FIG. 4)

Then, Ve was determined and from the value found and equation (2), the average molecular weight of the pulp was found to be 500,000 and that of CMC to be 61,100.

It is thus clear that the GPC determination of molecular weight and molecular weight distribution can be carried out under the same conditions for pulp and CMC.

Example 3

To evaluate the reproducibility of GPC determination, the GPC analysis of the CMC sample of 0.0003 g/ml concentration as prepared in Example 1 was carried out under the same conditions in 5 replicates. The results are shown in Table 2.

TABLE 2

| Replicate | Retention time (min.) | Flow rate (ml/min.) | Average molecular weight M* |
| --- | --- | --- | --- |
| 1 | 50.90 | 0.35 | 64,300 |
| 2 | 50.83 | 0.35 | 65,800 |
| 3 | 50.97 | 0.35 | 63,000 |
| 4 | 50.87 | 0.35 | 64,900 |
| 5 | 50.92 | 0.35 | 64,000 |
| Mean | | | 64,400 |
| Standard deviation | | | 900 |
| Coefficient of variation | | | 1.4% |

M*: the average molecular weight calculated from equation (2) (see below) and Ve (Log M = 11.40 − Ve)

It is clear from Table 2 that the reproducibility of the determination according to this invention is very high with a variation coefficient of 1.4%.

Example 4

To investigate the influence of column geometry on the accuracy of the molecular weight data generated by GPC, the GPC analysis of the CMC sample of 0.0003 g/ml concentration as prepared in Example 1 was carried out using the same mobile phase solvent as used in Example 1 under the following conditions in 5 replicates and the data were compared with the data generated in Example 3. These data are presented in Table 4.

TABLE 3

| | Example 3 | Example 4 |
| --- | --- | --- |
| Column | TSK gel GMPW | TSK gel GMPW |
| Column geometry | 1:80 | 1:50 |
| Flow rate | 0.35 ml/min. | 0.35 ml/min. |
| Injection size | 1 ml | 1 ml |

TABLE 4

| | Example 3 | | Example 4 | |
| --- | --- | --- | --- | --- |
| Replicate | Retention time (min) | Average molecular weight M*1 | Retention time (min) | Average molecular weight M*2 |
| 1 | 50.90 | 64,300 | 32.55 | 63,100 |
| 2 | 50.83 | 65,800 | 32.48 | 64,900 |
| 3 | 50.97 | 63,000 | 32.49 | 64,700 |
| 4 | 50.87 | 64,900 | 32.44 | 65,900 |
| 5 | 50.92 | 64,000 | 32.53 | 63,500 |
| Mean | | 64,400 | | 64,400 |
| Standard deviation | | 900 | | 1,000 |
| Coefficient of variation | | 1.4% | | 1.6% |

*1 The equation (2) for calculation of average molecular weight: Log M = 11.40 − 0.37 Ve
*2 The equation (2) for calculation of average molecular weight: Log M = 10.61 − 0.51 Ve It is apparent from Table 4 that the reproducibility of determination according to this invention is very high with a variation coefficient of 1.6%.

Example 5

The GPC determination of molecular weight was performed using the same mobile phase solvent as in Example 1 at a flow rate of 0.1 ml/min. Thus, the CMC sample of 0.0003 g/ml concentration as prepared in Example 1 was analyzed under the conditions set forth in Table 5 in 5 replicates and the data were compared with the data generated in Example 3. These data are presented in Table 6.

TABLE 5

|  | Example 3 | Example 4 |
|---|---|---|
| Column | TSK gel GMPW | TSK gel GMPW |
| Column geometry | 1:80 | 1:80 |
| Flow rate | 0.35 ml/min. | 0.35 ml/min. |
| Injection size | 1 ml | 1 ml |

TABLE 6

|  | Example 3 | | Example 5 | |
|---|---|---|---|---|
| Replicate | Retention time (min) | Average molecular weight M*[1] | Retention time (min) | Average molecular weight M*[2] |
| 1 | 50.90 | 64,300 | 153.28 | 64,700 |
| 2 | 50.83 | 65,800 | 154.22 | 62,200 |
| 3 | 50.97 | 63,000 | 152.61 | 66,500 |
| 4 | 50.87 | 64,900 | 152.06 | 68,100 |
| 5 | 50.92 | 64,000 | 153.94 | 63,000 |
| Mean |  | 64,400 |  | 64,900 |
| Standard deviation |  | 900 |  | 2,200 |
| Coefficient of variation |  | 1.4% |  | 3.4% |

*[1]The equation (2) for calculation of average molecular weight: Log M = 11.40 − 0.37 Ve
*[2]The equation (2) for calculation of average molecular weight: Log M = 7.57 − 0.18 Ve It is apparent from Table 6 that the reproducibility of determination in this example was slightly inferior to that found in Example 3 but was still satisfactory.

Example 6

The CMC sample of 0.0003 g/ml concentration as prepared in Example 1 was analyzed for molecular weight by GPC using the same mobile phase solvent as used in Example 1 and under the column geometry and other conditions set forth in Table 7 in 5 replicates. The results are shown in Table 8.

TABLE 7

|  | Example 3 | Example 6 |
|---|---|---|
| Column | TSK gel GMPW | TSK gel GMPW |
| Column geometry | 1:80 | 1:20 |
| Flow rate | 0.35 ml/min. | 0.35 ml/min. |
| Injection size | 1 ml | 1 ml |

TABLE 8

|  | Example 3 | | Example 6 | |
|---|---|---|---|---|
| Replicate | Retention time (min) | Average molecular weight M*[1] | Retention time (min) | Average molecular weight M*[2] |
| 1 | 50.90 | 64,300 | 13.00 | 62,100 |
| 2 | 50.83 | 65,800 | 12.95 | 65,500 |
| 3 | 50.97 | 63,000 | 12.96 | 64,900 |
| 4 | 50.87 | 64,900 | 12.90 | 69,200 |
| 5 | 50.92 | 64,000 | 12.92 | 67,800 |
| Mean |  | 64,400 |  | 65,400 |
| Standard deviation |  | 900 |  | 2,400 |
| Coefficient of variation |  | 1.4% |  | 3.7% |

*[1]The equation (2) for calculation of average molecular weight: Log M = 11.40 − 0.37 Ve
*[2]The equation (2) for calculation of average molecular weight: Log M = 10.89 − 1.34 Ve It is apparent from Table 8 that the reproducibility of determination in this example was slightly inferior to that found in Example 3 but was still satisfactory.

Example 7

Using the same mobile phase solvent as in Example 1, the GPC molecular weight determination was carried out on the CMC sample of 0.0003 g/ml as prepared in Example 1 under the column geometry and other conditions set forth in Table 9 in 5 replicates and the resulting data were compared with the data obtained in Example 3. These data are presented in Table 10.

TABLE 9

|  | Example 3 | Example 7 |
|---|---|---|
| Column | TSK gel GMPW | TSK gel GMPW |
| Column geometry | 1:80 | 1:150 |
| Flow rate | 0.35 ml/min. | 0.35 ml/min. |
| Injection size | 1 ml | 1 ml |

TABLE 10

|  | Example 3 | | Example 6 | |
|---|---|---|---|---|
| Replicate | Retention time (min) | Average molecular weight M*[1] | Retention time (min) | Average molecular weight M*[2] |
| 1 | 50.90 | 64,300 | 97.66 | 67,800 |
| 2 | 50.83 | 65,800 | 98.07 | 64,300 |
| 3 | 50.97 | 63,000 | 97.50 | 69,200 |
| 4 | 50.87 | 64,900 | 98.41 | 61,500 |
| 5 | 50.92 | 64,000 | 97.86 | 66,100 |
| Mean |  | 64,400 |  | 65,500 |
| Standard deviation |  | 900 |  | 2,500 |
| Coefficient of variation |  | 1.4% |  | 3.8% |

*[1]The equation (2) for calculation of average molecular weight: Log M = 11.40 − 0.37 Ve
*[2]The equation (2) for calculation of average molecular weight: Log M = 10.30 − 0.16 Ve It is apparent from Table 10 that the reproducibility of determination in this example was slightly inferior to that found in Example 3 but was still satisfactory.

What is claimed is:

1. A method of determining the molecular weight distribution of carboxymethylcellulose or a salt thereof by using gel permeation chromatography which comprises the steps of obtaining a sample by dissolving carboxymethylcellulose or a salt thereof in a solvent containing a metal-alkali, applying the sample to a column, eluting the sample from the column by flowing said solvent containing said metal-alkali through said column, analyzing the eluent, and determining the molecular weight distribution from the result of the analysis.

2. The method according to claim 1 wherein said metal-alkali is iron tartrate-sodium.

3. The method according to claim 1 wherein the column geometry in terms of the ratio of inside diameter to length is 1:40-100 and the flow rate through said column is 0.2-0.5 ml/min.

* * * * *